US006184500B1

(12) United States Patent
Glucksman

(10) Patent No.: US 6,184,500 B1
(45) Date of Patent: Feb. 6, 2001

(54) PARAFFIN BATH

(75) Inventor: Dov Glucksman, Wemham, MA (US)

(73) Assignee: HoMedics, Inc., Commerce Township, MI (US)

( * ) Notice: Under 35 U.S.C. 154(b), the term of this patent shall be extended for 0 days.

(21) Appl. No.: 09/523,506

(22) Filed: Mar. 10, 2000

(51) Int. Cl.7 ................................ A61F 7/00; A61K 7/50

(52) U.S. Cl. ............................ 219/432; 219/430; 607/86; 607/114

(58) Field of Search .................................... 219/432, 430, 219/433, 439; 4/493, 545; 607/85, 86, 96, 114

(56) References Cited

U.S. PATENT DOCUMENTS

| | | | | |
|---|---|---|---|---|
| 4,204,110 | * | 5/1980 | Smit et al. | 607/96 |
| 4,325,254 | * | 4/1982 | Svacina et al. | 607/114 |
| 4,485,297 | | 11/1984 | Grise et al. . | |
| 4,632,115 | * | 12/1986 | Bernardini | 607/86 |
| 4,656,339 | | 4/1987 | Grise . | |
| 4,696,303 | * | 9/1987 | Bernardini | 607/85 |
| 4,814,586 | | 3/1989 | Grise . | |
| 4,880,415 | * | 11/1989 | Urakami | 607/86 |
| 4,967,061 | * | 10/1990 | Weber, Jr. et al. | 219/438 |
| 5,674,268 | * | 10/1997 | Riazi | 607/96 |
| 5,700,284 | * | 12/1997 | Owens | 607/114 |

FOREIGN PATENT DOCUMENTS

| | | | |
|---|---|---|---|
| 61-65815 | * | 4/1986 | (JP) . |
| 11-56893 | * | 3/1999 | (JP) . |

OTHER PUBLICATIONS

TheraBath® Paraffin Wax Therapy for arthritis, bursitis, tendonitis, *www.lrehab.com/paraffin/index.htm*, May 23, 2000, pp. 1–3.

Remington Products, Hand Care, *www.remington–products.com/products/spatherapy/ahdn.html*, May 23, 2000, pp. 1–3.

Photographs of Gena Paraffin Bath Product, pp. 1–2.

* cited by examiner

*Primary Examiner*—Joseph Pelham
(74) *Attorney, Agent, or Firm*—Brooks & Kushman P.C.

(57) ABSTRACT

A paraffin bath apparatus for melting paraffin used in therapeutic applications is disclosed. The paraffin bath apparatus comprises a housing having a base, a sidewall and upper opening. An inner tub is formed of a temperature resistant polymeric material is a generally cup shaped member having a bottom wall, an upstanding wall and an open top. The inner tub is received within the upper opening of the housing with the bottom wall of the inner tub overlying the base of the housing. The heating element is located between the inner tub and the housing for providing heat to the inner tub sufficient to melt the paraffin but below the temperature that would adversely affect the polymeric material forming inner tub. A thermostatic sensor is disposed between the inner tub and the housing and is electrically connected to the heating element to control the heat provided to the inner tub. A temperature indicating element may be provided in the inner tub and placed in contact with paraffin melted in the inner tub. The temperature indicating element provides a visual indication that the paraffin in the tub is within a predetermined temperature range and is visible through the melted paraffin.

4 Claims, 3 Drawing Sheets

PARAFFIN BATH

TECHNICAL FIELD

The present invention relates to a therapeutic paraffin bath appliance.

BACKGROUND ART

Paraffin baths are used in therapeutic procedures, particularly procedures relating to the treatment of hand and foot treatments for arthritic and dermatologic conditions. In the treatment of arthritis or for moisturizing skin a person may be directed to place their hand or foot in a paraffin bath. In a paraffin bath, solid paraffin is heated to its melting point. The person may remove their hand or foot from the bath leaving a coating of paraffin applied to their skin. This procedure can relieve arthritic pain. This procedure may also be used for moisturizing the skin on a person's hand or foot.

Paraffin baths are normally provided with a metallic inner tub that is received in an outer housing with heating elements attached to or located adjacent the metallic inner tub. Paraffin baths having a metallic inner tub are relatively costly to manufacture which adds to the ultimate cost to consumers of such units.

An important aspect of paraffin bath appliances is the heating control. some prior art paraffin baths have been provided with a costly electronic controller.

The heating system should be failsafe in that it should not be permitted to overheat. Prior art paraffin baths do not have a temperature indicator reflecting the temperature of the melted paraffin. Another disadvantage of some prior art paraffin baths is that a thermostat could possibly fail or the unit may be subject to temperature fluctuation or nonuniform heating of the paraffin in the bath.

When the paraffin bath is not in use, it is desirable to protect the paraffin from becoming contaminated.

These and other disadvantages encountered by prior art paraffin baths are addressed by the paraffin bath made according to the present invention as will be understood from the following summary of the invention.

DISCLOSURE OF INVENTION

A therapeutic paraffin bath designed for use by consumers, medical offices or physical therapy clinics is preferably durable and reliable as well as being easy to operate. A paraffin bath should also have a rapid heating capability so that it is not necessary to wait for an extended period of time for the paraffin to melt and reach the desired temperature for treatment.

It is also preferable to provide temperature control within a range of potential treatment temperatures. According to the invention, a simple failsafe temperature indicator is provided that permits a consumer or health professional to directly read the temperature of the paraffin in the bath.

The therapeutic paraffin bath preferably includes dual heating elements that are capable of rapidly heating the paraffin in the bath. Even heating of the paraffin prevents hot spots and cold spots within the bath.

The temperature control is preferably provided by a reliable and inexpensive adjustable thermostat. The thermostat preferably is provided with a conductor strip through which temperature is monitored. A thermostatic fuse is also preferably provided as a safety mechanism in event that the thermostat control fails or the unit overheats. The thermostatic fuse would open if a overheating condition is sensed and cuts off power to the paraffin bath heating elements.

The therapeutic paraffin bath of the present invention preferably includes a plastic inner tub that is heated by means of two separate heating elements. The heating elements are a rope type, or braided, heating elements sandwiched in aluminum foil. One heating element extends about the perimeter of the plastic inner tub. A second heating element is provided in the floor of the unit adjacent the bottom of the inner tub.

A removable strainer is preferably provided that may be placed on the bottom of the inner tub. The strainer prevents direct contact with the bottom wall of the inner tub and also functions to obscure dirt or skin particles that may be otherwise visible in the bottom of the paraffin bath.

The therapeutic paraffin bath of the present invention preferably includes a lid that may be locked in place over the inner tub. The lid is preferably mechanically locked to the inner tub of the paraffin bath as the bath is heated or when the bath is transported.

According to the invention, a paraffin bath apparatus for melting paraffin is provided. A paraffin bath includes a housing having a base, a sidewall and an upper opening. An inner tub is formed of polymeric material that is selected for high temperature performance and is generally cup shaped having a bottom wall, an upstanding wall and an open top. The inner tub is received within the upper opening of the housing with the bottom wall overlying the base. Paraffin is supplied in the inner tub. The heating element is disposed between the inner tub and the housing. The heating element provides heat through the inner tub sufficient to melt the paraffin but below the temperature that would adversely affect the polymeric material forming the inner tub. An adjustable thermostatic sensor is disposed between the inner tub and the housing that is electrically connected to the heating element to control the heat provided to the inner tub. A thermal fuse is electrically connected to a circuit including the heating elements. The thermal fuse disables the heating elements when the temperature of the space between the housing and the inner tub exceeds a predetermined temperature.

The heating element may also include a base heating element located between the base and the bottom wall and a side heating element located between the side wall and the upstanding wall. The base heating element and the side heating element are formed as separate parts. The heating elements are preferably braided metallic members. The braided metallic member is contained between two layers of foil that aid in dispersing heat. The thermostatic sensor is remotely mounted relative to the inner tub and is connected to a thermally conductive element that contacts a portion of the inner tub.

The inner tub is preferably of formed polypropylene but may also be formed of another temperature resistant polymer.

The present invention may also be characterized as a paraffin bath apparatus for melting paraffin that is provided with a temperature indicating element indicating the temperature of the paraffin melted in the apparatus. A housing having a base and an upper opening receives an inner tub that is generally cup-shaped and has a bottom wall and an open top. The inner tub is received within the upper opening of the housing with the bottom wall of the inner tub overlying the base. Paraffin is supplied to the inner tub for melting. A heating element is disposed between the inner tub and housing. The adjustable thermostatic sensor is disposed between the inner tub and the housing. The temperature indicating element is disposed in the inner tub and placed in contact with paraffin in the inner tub at a location that is not directly opposite a heating element. The temperature indicating element provides a visual indication that the paraffin in the inner tub is within a predetermined temperature range. The visual indication is visible through the paraffin after the paraffin is melted.

The temperature indicating element is preferably secured to a strainer that is disposed in the tub on the bottom wall. The temperature indicating element may alternatively be secured to the inside of the inner tub at a location that is not directly opposite a heating element. The temperature indicating element is a color changing strip that includes a chemical that changes colors to indicate that the paraffin is within the predetermined temperature range.

These and other aspects and objects of the present invention will be more clearly understood in view of the attached drawings and in light of the following detailed description of the invention.

BEST MODE FOR CARRYING OUT THE INVENTION

Figure 1:
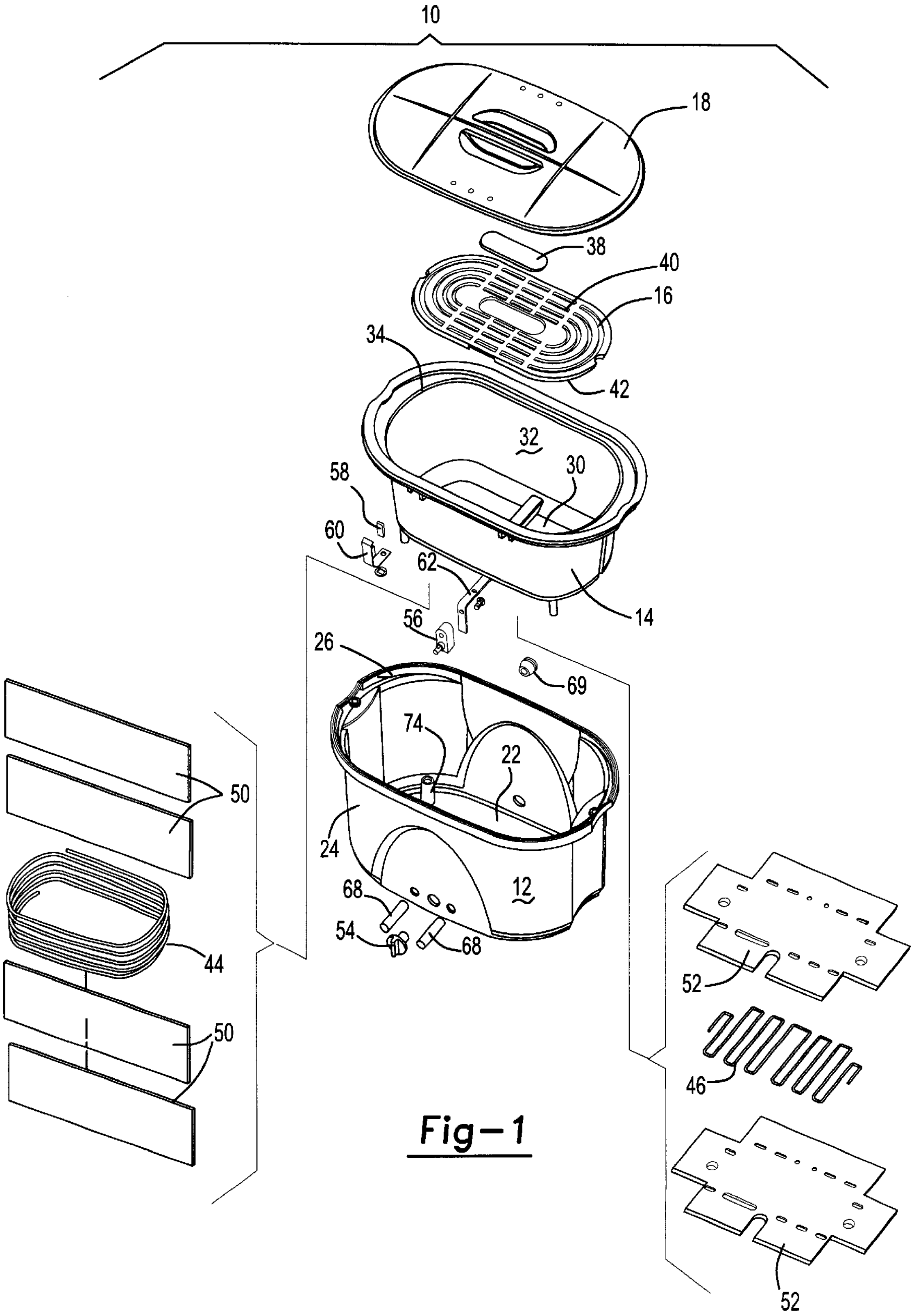
FIG. 1 is an exploded perspective view of a paraffin bath made in accordance with the present invention.
Figure 2:
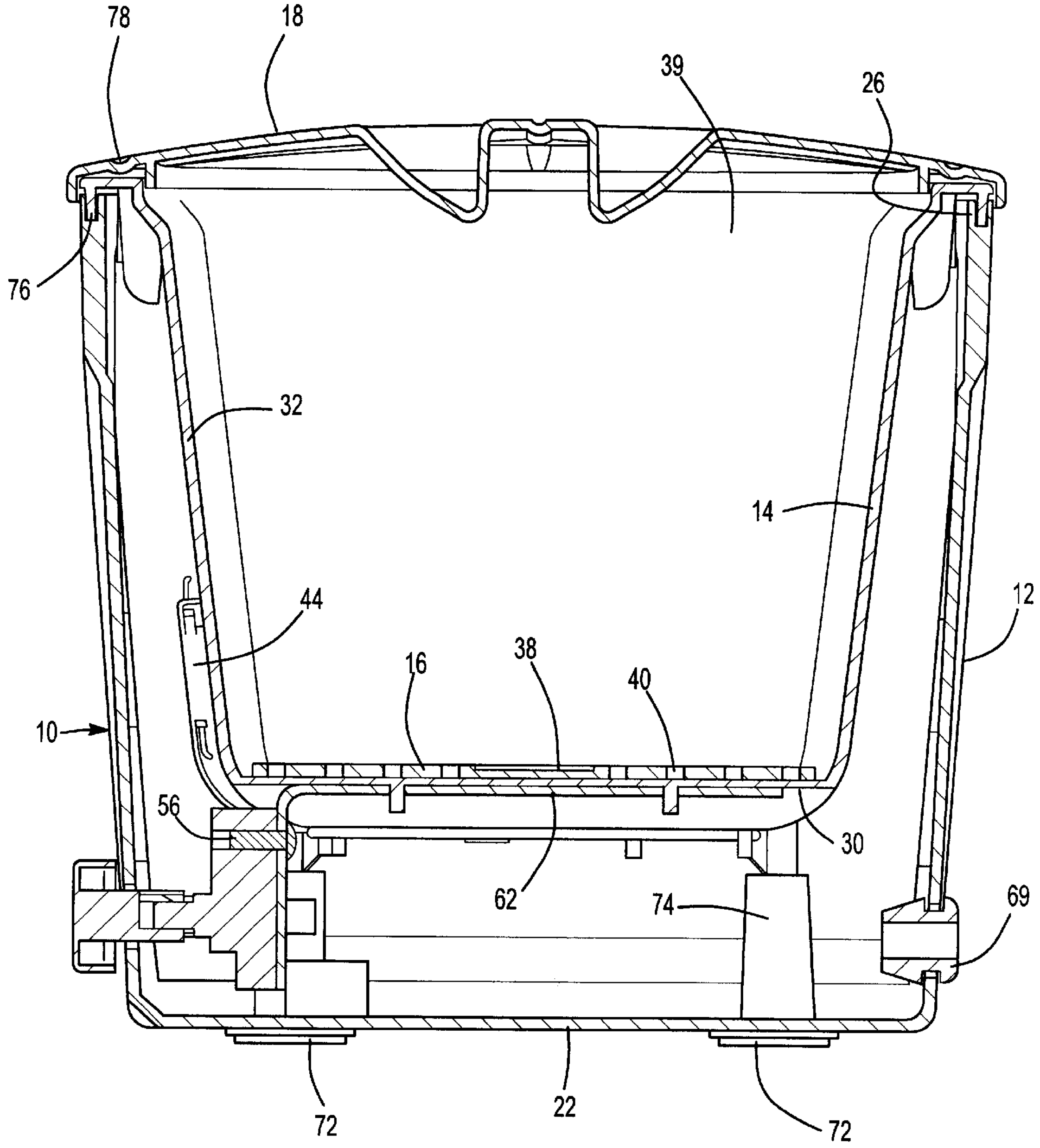
FIG. 2 is a transverse cross-sectional view taken through the center of the paraffin bath shown in FIG. 1.
Figure 3:
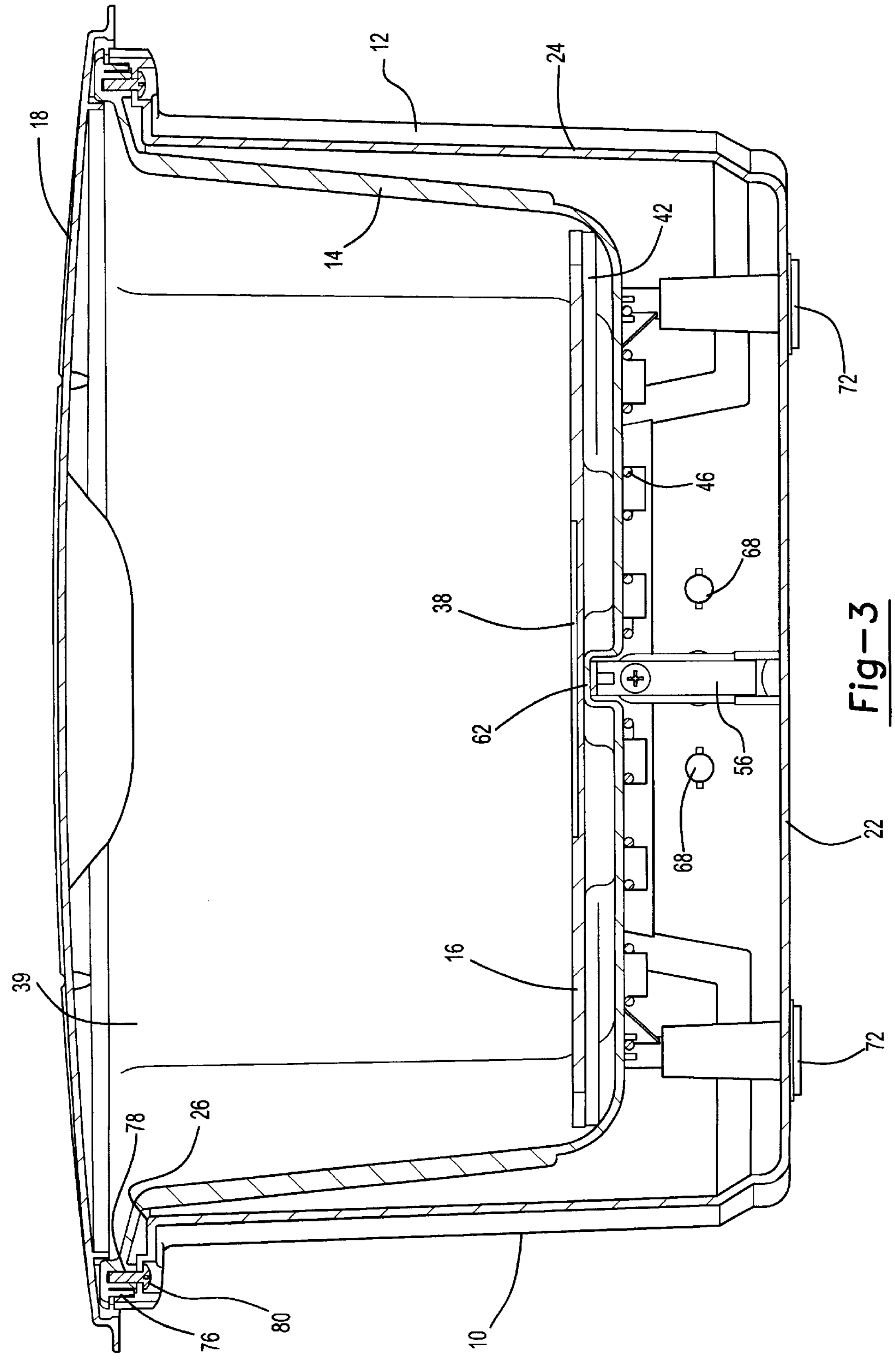
FIG. 3 is a longitudinal cross-sectional view taken through the center of the paraffin bath.

Referring now to FIG. 1, a paraffin bath appliance 10 of the present invention is shown in an exploded perspective view. Assembly of the paraffin bath appliance is shown in FIGS. 2 and 3. The principal structural components of the paraffin bath appliance 10 include a housing 12 in which an inner tub 14 is received. A strainer 16 is loosely located in the inner tub 14. A lid 18 is provided to cover the inner tub 14.

The housing 12 includes a base 22 and a side wall 24 extending around the periphery of the base 22. The housing defines an upper opening 26 on its upper end.

The inner tub 14 is preferably formed of a high temperature resistant polymeric material such as polypropylene. the inner tub 14 has a bottom wall 30 and an upstanding wall 32 extending upwardly from the periphery of the bottom wall 30. The upstanding wall 32 defines an open top 34 at its upper end.

A temperature indicating element 38 is provided on the strainer 16. The temperature indicating element 38 is formed of a polymeric material having a material contained therein that changes color when a predetermined temperature is reached. The strainer 16 has a plurality of slots 40 that permit paraffin to circulate through the strainer 16. Any dirt, skin particles or other debris fall through the slots 40 to the bottom of the inner tub 14. Flanges 42 extend downwardly from portions of the periphery of the strainer 16 that hold the strainer 16 in a spaced relationship relative to the bottom wall 30 of the inner tub 14.

Side heating element 44 extends in a helical fashion around the upstanding wall 32 of the inner tub 40. The heating element 44 is located within the housing 12 adjacent the side wall 24. A base heating element 46 is arranged in a serpentine fashion between the base 22 and bottom wall 30 and is secured to the bottom wall 30 of the inner tub 14. Side foil sheets 50 are provided on the inner and outer sides of the side heating element 44. Base foil sheets 52 are provided on the upper and lower surfaces of the base heating element 46. The side heating element 44 and base heating element 46 are preferably formed of a braided metal of preferably copper or aluminum that is durable and long lasting. The side and base foil sheets 50 and 52 are provided to evenly distribute the heat generated by the side and base heating elements 44 and 46 around and under the inner tub 14.

A knob 54 for an adjustable thermostat 56 may be turned by a user to control the temperature of the paraffin in the paraffin bath appliance 10. The adjustable thermostat 56 is provided to control the heating process and provide a mechanism for sensing the temperature of the inner tub 14.

A thermal fuse 58 is provided in the electrical circuit including the side and base heating elements 44 and 46 so that if the temperature within the housing 12 exceeds an upper limit the current supplied to the heating elements 44 and 46 will be interrupted. The thermal fuse 58 is received in a thermal fuse clip 60 and is preferably replaceable so that the unit may be serviced. Conductive element 62 is a metal strip selected for its thermally conductive properties and is secured to the bottom wall 30 of the inner tub 40 to sense the temperature of the inner tub 14 and provide a thermal input to the thermostat 56 that is slightly spaced from the inner tub 14 and mounted on the housing 12.

A strain relief 64 is provided in the rear of the side wall 24. The strain relief 64 is provided to protect and retain the power cord.

Lights 68 are provided between the housing 12 and inner tub 14 on the front portion of the side wall 24 with one indicating that the bath is turned on and the other indicating that the thermostat has opened indicating that the bath is at the desired temperature.

Referring now to FIGS. 2 and 3, the assembled paraffin bath appliance 10 is shown in transverse and longitudinal cross-sections, respectively. The housing 12 has rubber feet 72 on the bottom of the base 22. The feet are located at the base of faster receiving posts 74.

A downwardly extending flange 76 extends about the open top 34 of the inner tub 14. The flange 76 is received in a top groove 78 formed about the upper opening 26 of the housing 12. The flange 76 and groove 78 form a seal between the housing 12 and the inner tub 14. Screws 80 are provided to securely fasten the housing 12 and inner tub 14 together.

While not shown, electrical wires connect the thermostat 56, thermofuse 58, heating elements 44, 46 and lights 68 in a conventional circuit.

In an alternative embodiment, temperature indicating element 38 could be affixed to the inner tub 14 on the side wall 24 thereof. The temperature indicating element 38 should be preferably located on a portion of the upstanding wall 32 that is not directly opposite the side heating element 44. Heat radiated by the heating element should not be allowed to distort the indication provided by the temperature indicating element 38 that is intended to sense the temperature of the paraffin in the inner tub 14.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A paraffin bath apparatus for melting paraffin comprising:

a housing being generally cup shaped and having a base and an upper opening;

an inner tub being generally cup shaped and having a bottom wall and an open top, the inner tub being received within upper opening of the housing with the bottom wall overlying the base, wherein paraffin is supplied in the inner tub;

a heating element disposed between the inner tub and the housing; and a temperature indicating element disposed in the inner tub and placed in contact with paraffin in the inner tub, the temperature indicating element providing a visual indication that the paraffin in the inner tub is within a predetermined temperature range, the visual indication being visible through the paraffin after it is melted.

2. The paraffin bath apparatus of claim 1 further comprising a strainer disposed within the inner tub on the bottom wall, the temperature indicating element being secured to the strainer.

3. The paraffin bath apparatus of claim 1 further comprising the temperature indicating element being secured to the inside of the inner tub.

4. The paraffin bath apparatus of claim 1 further comprising the temperature indicating element being a color changing strip that includes a chemical that changes color to indicate that the paraffin is within the predetermined temperature range.

* * * * *